US012728099B2

(12) United States Patent
Maretti et al.

(10) Patent No.: US 12,728,099 B2
(45) Date of Patent: Sep. 8, 2026

(54) FORMULATION TO DELIVER LIPOPHILIC ACTIVE INGREDIENTS

(71) Applicant: PERFORMS S.R.L., Modena (IT)

(72) Inventors: Eleonora Maretti, Modena (IT); Eliana Grazia Leo, Modena (IT); Virginia Brighenti, Modena (IT)

(73) Assignee: PERFORMS S.R.L., Modena (IT)

( * ) Notice: Subject to any disclaimer, the term of this patent is extended or adjusted under 35 U.S.C. 154(b) by 602 days.

(21) Appl. No.: 18/011,639

(22) PCT Filed: Jul. 7, 2021

(86) PCT No.: PCT/IB2021/056096
§ 371 (c)(1),
(2) Date: Dec. 20, 2022

(87) PCT Pub. No.: WO2022/009118
PCT Pub. Date: Jan. 13, 2022

(65) Prior Publication Data
US 2023/0255893 A1 Aug. 17, 2023

(30) Foreign Application Priority Data
Jul. 7, 2020 (IT) ........................ 102020000016411

(51) Int. Cl.
*A61K 9/51* (2006.01)
*A61K 9/00* (2006.01)
*A61K 31/164* (2006.01)
*A61K 31/232* (2006.01)
*A61P 17/06* (2006.01)

(52) U.S. Cl.
CPC .......... *A61K 9/5192* (2013.01); *A61K 9/0014* (2013.01); *A61K 9/5123* (2013.01); *A61K 31/164* (2013.01); *A61K 31/232* (2013.01); *A61P 17/06* (2018.01)

(58) Field of Classification Search
CPC ... A61K 9/5123; A61K 9/0014; A61K 31/164
See application file for complete search history.

(56) References Cited

U.S. PATENT DOCUMENTS 4,284,630 A * 8/1981 Yu .......................... A61K 47/02 514/180
2010/0228013 A1* 9/2010 Suzuki .................. A61K 36/06 435/74
2011/0046225 A1* 2/2011 Dalle Carbonare .... A61P 17/10 514/625
2013/0237613 A1* 9/2013 Kim ......................... A61K 8/60 514/777
2015/0111969 A1 4/2015 Van Dross et al.
2017/0020896 A1* 1/2017 Kelidari ............... A61K 31/585

FOREIGN PATENT DOCUMENTS

WO WO-2019123417 A1 * 6/2019 ........... A61K 31/573

OTHER PUBLICATIONS

Tronino et al (Colloids and Surfaces B: Biointerfaces, 2016, vol. 141, pp. 311-317) (Year: 2016).*
An Office Action in the corresponding Saudi Arabian patent application No. 522441724.
Van Zuuren, Esther J., et al. "Emollients and moisturisers for eczema" Cochrane Database of Systematic Reviews 2 (2017).
Patel, Vishal R., and Y. K. Agrawal. "Nanosuspension: An approach to enhance solubility of drugs." Journal of advanced pharmaceutical technology & research 2.2 (2011): 81.
Patravale, V. B., Abhijit A. Date, and R. M. Kulkarni. "Nanosuspensions: a promising drug delivery strategy." Journal of pharmacy and pharmacology 56.7 (2004): 827-840.
International Search Report and Written Opinion for PCT/IB2021/056096, mailed Oct. 28, 2021.
Tronino, D. et al., Nanoparticles prolong N-palmitoylethanolamide anti-inflammatory and analgesic effects in vivo, Colloids and Surfaces B: Biointerfaces, vol. 141, 311-317, Feb. 2016.
Goodman, M.B. et al., Case Series: N-Palmitoylethanolamide Cream (PEA or MIMYX) Used as an Adjunct to Prevent Inverse Psoriasis Flare Frequency, Journal of the American Osteopathic College of Dermatology, 11(1), 49-50, Jul. 2008.
Journal of the American Osteopathic College of Dermatology, Contents, 11(1), p. 4, Jul. 2008.
Retrieved from the Internet: URL:drugsdepot.com, Oct. 2021.
Beggiato, S. et al., Palmitoylethanolamide (PEA) as a Potential Therapeutic Agent in Alzheimer's Disease, Frontiers in Pharmacology, vol. 10, Article 821, Jul. 2019.
Huang et al., Biological and Pharmacological Activities of Squalene and Related Compounds: Potential Uses in Cosmetic Dermatology, MDPI Journal, Molecules 2009, ISSN 1420-30249, Jan. 2009, Switzerland.
Impellizzeri D et al., "Micronized/ultramicronized palmitoylethanolamide displays superior oral efficacy compared to nonmicronized palmitoylethanolamide in a rat model of inflammatory pain", Journal of Neuroinflammation 2014, 11:136.
Office Action issued Feb. 3, 2026 in connection with counterpart Japanese application No. 2023-501648.

* cited by examiner

*Primary Examiner* — Mark V Stevens
(74) *Attorney, Agent, or Firm* — Silvia Salvadori, P.C.; Silvia Salvadori

(57) ABSTRACT

The present invention relates to a technological platform for the delivery of lipophilic active ingredients.

18 Claims, 8 Drawing Sheets

FORMULATION TO DELIVER LIPOPHILIC ACTIVE INGREDIENTS

CROSS-REFERENCE TO RELATED APPLICATIONS

This application is a national phase application of PCT/IB2021/056096, filed on Jul. 7, 2021, which claims the benefit of Italian Application No. 102020000016411, filed Jul. 7, 2020, both of which are incorporated by reference herein in their entirety.

TECHNICAL FIELD OF THE INVENTION

The present invention finds application in the medical, pharmaceutical, nutraceutical, and cosmetic fields and, in particular, relates to a novel platform for the delivery of active ingredients.

STATE OF THE ART

PEA (whose structure is shown in FIG. 1) is the amide between palmitic acid and ethanolamine, which is abundant in the central nervous system.

PEA is produced conspicuously by glial cells and is an important mediator that acts both centrally and peripherally.

Palmitoylethanolamide (PEA) is produced in the body to fight pain and inflammation. Many animals and plants also produce PEA. The highest amounts may be found in soy lecithin, soybeans, egg yolk, and peanuts. This fatty acid may increase endogenous cannabinoids and protect nerves throughout the body.

Its benefits are encouraging for a wide range of difficult-to-treat disorders.

About 25 years ago, it was discovered that one of its structural analogs, anandamide (AEA), was the endogenous ligand of cannabinoid receptors, the target of the Δ9-tetrahydrocannabinol, found in marijuana.

In addition to its well-known anti-inflammatory activity, PEA is able to induce analgesia, to exert a neuroprotective effect, to inhibit food intake, to reduce intestinal motility and the proliferation of cancer cells, and to protect the vascular endothelium in case of cardiac ischemia.

Other studies showed that this endogenous acylethanolamide was able to inhibit mast cell degranulation and inflammation at the peripheral level, effects that were accompanied by changes in nitric oxide production by macrophages and in the expression of proinflammatory proteins, such as inducible nitric oxide synthase (iNOS) and cyclooxygenase-2 (COX-2).

PEA has been shown to bind to a receptor in the cell nucleus (a nuclear receptor) and to exert a wide variety of biological functions related to chronic pain and inflammation. Peroxisome proliferator-activated receptor alpha (PPAR-$\alpha$) is thought to be the primary target. However, the presence of palmitoylethanolamide, and other structurally related N-acyl ethanolamines, is known to enhance the activity of anandamide through a so-called "entourage effect."

PEA is also able to attenuate the degree of inflammation in an animal model of peripheral injury, chronic constriction injury, which is a model of neuropathy associated with a profound inflammatory response involving T cells and macrophages. After nerve injury, PEA reduces edema and macrophage infiltration, assessed by the amount of CD86+ cells, which are responsible for the production of high levels of nitric oxide, superoxide radicals, and pro-inflammatory cytokines.

Therefore, the anti-hyperalgesic and neuroprotective properties of PEA are related not only to its anti-inflammatory effects and its ability to prevent macrophage infiltration into the nerve. Taken together, this evidence suggests a key role for PEA in maintaining cellular homeostasis during pathological stimuli that cause the inflammatory response and tissue damage.

Despite its clinical potential, PEA and all endocannabinoids have serious solubilization difficulties.

PEA is practically insoluble in water, oils, and most common organic solvents. PEA is poorly soluble in methanol, ethanol, and isopropyl alcohol.

The PEA on the market is used orally as a dietary supplement in very high dosages (600 mg per dose) also in micronized form.

U.S. Patent Application US 2011/046225 describes the use of a mixture of palmitoylethanolamide and stearylethanolamide for the synergistic treatment of conditions that may benefit from the endocannabinoid-type properties of these compounds.

The publication by Diana Tronino et al ("Nanoparticles prolong N-palmitoylethanolamide anti-inflammatory and analgesic effects in vivo," COLLOIDS AND SURFACES B:BIOINTERFACES, VOL. 141, 1 Feb. 2016, pages 311-317, XP029465877) describes Compritol ATO (behenic acid triglycerides, HLB2) nanoparticles wherein palmitoylethanolamide is incorporated using miglyol (medium chain triglycerides, MCTs) and Lutrol F68 (high HLB surfactants). The preparation is obtained by hot homogenization after having previously melted the lipids and dissolved the palmitoylethanolamide in the melted lipids.

The prior art document CN 108 451 905 B describes a gambogic acid nanoemulsion obtained through the use of two stabilizing surfactants.

SUMMARY OF THE INVENTION

The inventors of the present patent application have developed a technological platform for preparing nanoscale formulations of water-insoluble compounds.

Said platform has been in particular utilized for the formulation of active ingredients with very low solubility.

BRIEF DESCRIPTION OF THE DRAWINGS

Figure 1:
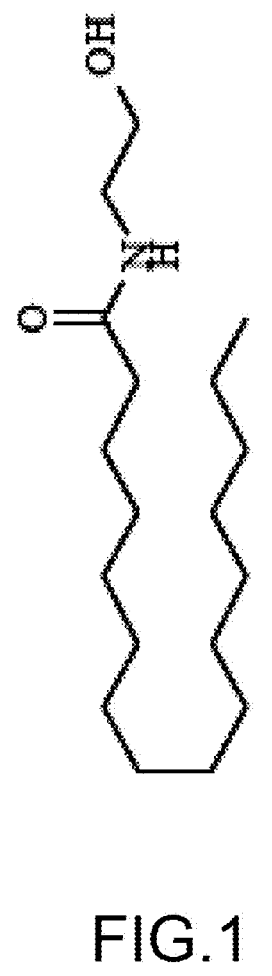

FIG. 1 shows the formula for palmitoylethanolamide.

SUBJECT MATTER OF THE INVENTION

Figure 2:
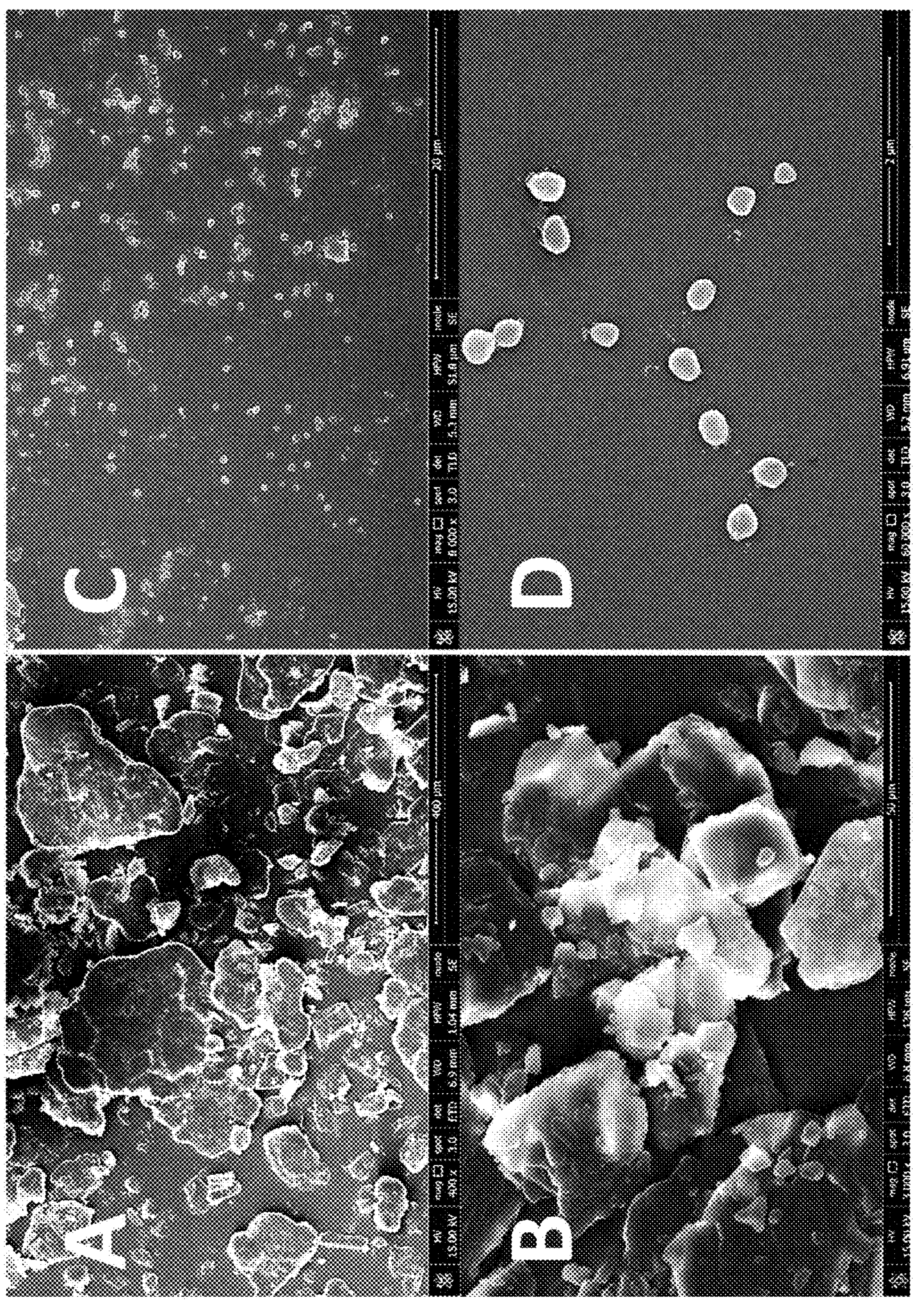
FIG. 2 shows scanning electron microscopy images at different magnifications of raw PEA (sx; A=400×, B=3,000×) and a formulation according to the present invention (dx; C=8,000×, D=60,000×).

A first subject of the present invention is represented by a process for preparing a formulation for delivering an active ingredient.

In a preferred aspect of the invention, the active ingredient is lipophilic.

A second subject is represented by a formulation obtained according to the process of the invention.

A third subject of the invention is represented by pharmaceutical or nutraceutical or cosmetic preparations comprising the described formulation.

A fourth subject of the invention is represented by the medical use of the formulation of the invention.

In a preferred aspect of the invention, the medical use is described for the treatment of conditions selected from the group comprising: psoriasis, dermatitis, eczema, acne, folliculitis, pityriasis.

In a further aspect of the present invention, the medical use is described for the treatment of conditions selected from the group comprising: pulmonary infection and inflammation, atherosclerosis, asthma, rheumatoid arthritis, multiple sclerosis, neurodegenerative diseases, Crohn's disease, colitis, and glaucoma.

In a further aspect, the formulations or preparations of the invention are described for cosmetic and nutraceutical use.

In a fifth subject of the invention, a method is described for treating conditions selected from the group comprising: psoriasis, dermatitis, eczema, acne, folliculitis, pityriasis.

DETAILED DESCRIPTION OF THE INVENTION

A first subject of the present invention is represented by a process for preparing a formulation for delivering an active ingredient.

For the purposes of the present patent application, said active ingredient is preferably lipophilic.

In a particularly preferred aspect, said active ingredient is palmitoylethanolamide.

In particular, the process of the invention comprises the steps of:

1) dissolving the lipophilic active ingredient in a solvent miscible with water in the presence of squalene and a first surfactant.

2) dropping the resulting solution in an aqueous phase in the presence of a second surfactant.

In one particular aspect, the lipophilic active ingredient delivered is a derivative of arachidonic acid or ethanolamide.

For the purposes of the present invention, the active ingredient may be one of the endocannabinoids or it may not be one of the endocannabinoids.

This active substance of lipophilic nature may be selected from the group comprising: oleoylethanolamide (OEA), anandamide (AEA), 2-arachidonoylglycerol (2-AG), stearoylethanolamide (SEA), docosahexaenoylethanolamide (DHEA), linoleoyl ethanolamide (LEA), adelmidrol.

In step 1) the lipophilic active ingredient is preferably palmitoylethanolamide.

In one aspect of the present invention, the solvent employed is selected from the group comprising: ethanol, methanol, isopropanol, acetone, acetonitrile.

In one aspect of the present invention, the first surfactant used in step 1) is a surfactant having HLB<10.

In a preferred aspect of the invention, said first surfactant is glycerylmonostearate (GMS) or sorbitan monostearate.

In one aspect of the invention, the solution of step 1) is obtained by employing concentrations of the lipophilic active ingredient of about 0.05-5% (w/v).

In one aspect of the invention, the solution of step 1) is obtained by employing squalene concentrations of about 0.05-5% (w/v).

Regarding step 2), the second surfactant used is a surfactant having HLB≥10.

For the purposes of the present invention, the second surfactant is selected from the group comprising: a triterpenoid saponin or a mixture thereof, polysorbates, poloxamer, gelatin, polyethylene glycol derivatives, sucrose palmitate.

In a preferred aspect of the invention, said surfactant is sucrose palmitate.

In one aspect of the invention, step 2) is conducted under mechanical stirring.

The solvent of step 2) is preferably water.

According to a preferred aspect of the present invention, the surfactant of step 1) and the surfactant of step 2) are added in a total amount by weight whereby a ratio of about 1:0.25-1:1.75 lipophilic active ingredient:total surfactants is obtained (i.e.: weight of surfactant of step 1)+weight of surfactant of step 2)).

Thus, in a particular aspect of the present invention, the surfactant of step 1) and the surfactant of step 2) are added in a total amount by weight whereby a ratio of about 1:0.25 to 1:1.75 PEA:total surfactants is obtained (i.e.: weight of surfactant of step 1)+weight of surfactant of step 2)).

After step 2), the mixture is left to evaporate until the solvent is completely evaporated.

In one aspect of the invention, the evaporation is achieved by magnetic stirring.

In one aspect of the present invention, in step 2) a compound is subsequently added selected from:

- mannose or its derivatives in monomeric, oligomeric, and polymeric forms; or
- fucose or its derivatives in monomeric, oligomeric, and polymeric forms.

For the purposes of the present invention, mannose derivatives include, for example: methyl alpha-D-mannopyranoside or mannosylated compounds selected from, for example, the group comprising: fatty acids, proteins, or N-acetylglucosamine.

For the purposes of the present invention, fucose derivatives include, for example fucosylated compounds selected from the group comprising: fatty acids, proteins, or N-acetylglucosamine.

In a preferred aspect of the invention, fucose is added.

In one aspect of the present invention, mannose or fucose or a derivative thereof is added in a 1:1 molar ratio relative to the hydrophilic surfactant.

The formulation obtained according to the present invention is of the nanostructured type.

This means that the process leads to the formation of a nanostructured PEA suspension.

In particular, the obtained nanostructured PEA suspension has a size, determined by light scattering, of about 200-350 nm, preferably about 280-320 nm and more preferably about 290-310 nm or about 300 nm.

As noted above, the process of the present patent application may be carried out for obtaining nanostructured formulations to deliver a lipophilic active ingredient.

In one particular aspect, the lipophilic active ingredient delivered is a derivative of arachidonic acid or ethanolamide.

For the purposes of the present invention, the active ingredient may be one of the endocannabinoids or it may not be one of the endocannabinoids.

Said lipophilic active ingredient may be selected from the group comprising: oleylethanolamide (OEA), anandamide (AEA), 2-arachidonoylglycerol (2-AG), stearoylethanolamide (SEA), docosahexaenoylethanolamide (DH EA), linoleoylethanolamide (LEA), adelmidrol.

A second subject of the invention is a formulation obtained according to the process described above.

Such a formulation is preferably a suspension or a dry powder.

In a preferred aspect, the described formulation comprises PEA in a nanostructured form in a concentration of about 0.3-1.5% (w/v).

A third subject of the invention is a pharmaceutical or cosmetic preparation comprising the described formulation.

For the purposes of the present invention, said preparation is prepared to be administered by cutaneous, oral, ocular, inhalation, systemic (intravenous, intramuscular, or subcutaneous or intra-articular) routes.

For example, the preparation of the invention may be in one of the following forms: cream, gel, spray, emulsion, foam, dry powder or suspension for inhalation, capsule, tablet, granules, suppository, eye drops, aqueous suspension, transdermal patch.

A fourth subject of the invention is the medical use of the formulation or preparation of the invention.

In a preferred aspect of the invention, the medical use is described for the treatment of conditions selected from the group comprising: psoriasis, dermatitis, eczema, acne, folliculitis, pityriasis.

According to a further aspect of the present invention, the medical use is described for the treatment of conditions selected from the group comprising: pulmonary infections and inflammations, atherosclerosis, asthma, rheumatoid arthritis, multiple sclerosis, neurodegenerative diseases, Crohn's disease, colitis, and glaucoma.

Specifically, the formulation of the invention is administered topically for a period of 14 days twice daily.

According to a further subject, the formulations or preparations of the invention according to the foregoing are described for cosmetic and nutraceutical use.

According to a fifth subject of the invention, a method is described for treating a condition selected from the group comprising: psoriasis, dermatitis, eczema, acne, folliculitis, pityriasis, pulmonary infections and inflammations, atherosclerosis, asthma, rheumatoid arthritis, multiple sclerosis, neurodegenerative diseases, Crohn's disease, colitis, and glaucoma comprising the step of administering to a patient suffering from such a condition a nanostructured formulation or a pharmaceutical or nutraceutical or cosmetic preparation of the invention.

In a preferred aspect, said administration is topical.

In a preferred aspect, said administration is repeated over a 14-day period. Said administration may be carried out twice daily.

Excluded from the purposes of the present patent application are the process, formulation, preparation, medical use, and method of treatment described above when the active ingredient is a compound belonging to the class of endocannabinoids and said first and said second surfactant are surfactants having a steroid (cyclopentanoperhydrophenanthrenic) structure.

The invention will be further described with reference to the following non-limiting examples of the present invention.

Example 1

Preparation of the Formulation

Palmitoylethanolamide (PEA), squalene and a first surfactant having HLB<10, were dissolved in ethanol, according to the quantitative ratios of the present invention. The resulting solution was dripped under agitation in an aqueous phase to which a second surfactant with HLB≥10 and a mannose derivative were added.

The resulting mixture was placed in agitation by electromagnetic stirring until the solvent was completely evaporated.

Example 2

Solubility Assays and Solubilization Rate

Solubility tests were performed on the suspension obtained according to Example 1 in comparison with raw PEA.

Solubility tests of raw PEA and nanostructured PEA of the present invention were performed in the following dissolution media:

- demineralized water,
- phosphate buffer pH 7.4,
- simulated intestinal fluid (pH 6.8), and
- simulated pulmonary fluid (pH 7.4)

to determine any change in solubility of the compound.

Solubility was measured at 25° C. in the different dissolution media under magnetic stirring after 24 hours. Specifically, an excess amount of raw PEA (17 mg) and Example 1 (6 mL, corresponding to 17 mg of nanostructured PEA) were added separately to the different solutions mentioned above to obtain a final volume of 12 mL. After 24 h, an aliquot was taken and filtered through a 0.2 μm syringe filter and finally analyzed by HPLC.

The data are shown in Table I below.

TABLE I

| | Raw PEA (μg/mL) | Example 1 (μg/mL) |
|---|---|---|
| MilliQ demineralized water | <0.1 | 16.76 ± 1.33 |
| Phosphate buffer pH 7.4 | 0.64 ± 0.05 | 15.51 ± 5.46 |
| Simulated intestinal fluid pH 6.8 | 0.22 ± 0.03 | 6.22 ± 1.73 |
| Simulated pulmonary fluid pH 7.4 | 0.80 ± 0.12 | 8.22 ± 0.09 |

To evaluate the change in dissolution rate, experiments were conducted using a 1% aqueous sodium cholate solution.

Starting with a suspension of 0.3 mg of raw or nanostructured PEA obtained according to Example 1 suspended in 10 mL of 1% w/v sodium cholate solution (final total concentration is 30 μg/mL), the dissolution rate of PEA was evaluated over time.

Dissolution data are shown in Table II.

TABLE II

| | PEA (μg/mL) | Example 1 (μg/mL) |
|---|---|---|
| 30 min | 3.31 ± 2.30 | 25.5 ± 1.43 |
| 1 hour | 4.56 ± 1.02 | 25.03 ± 2.36 |
| 2 hours | 6.15 ± 1.22 | 25.23 ± 2.66 |
| 4 hours | 8.61 ± 0.68 | 25.37 ± 2.70 |
| 6 hours | 9.31 ± 0.71 | 25.83 ± 0.18 |

HPLC Method

The PEA concentration in the solutions to be analyzed (Example 2) was determined by HPLC-UV/Vis analysis.

The system used is composed of two PU-2080 Plus pumps, a HG-980-30 solvent mixing module, a Degasys DG-1210 degassing module (Uniflows Co., Ltd., Tokyo, Japan) and a UV-VIS UV-2075 Plus detector. The data were recorded and processed using the Hercule Lite Chromatography Interface and Borwin Software (Jasco Corporation, Tokyo, Japan), respectively. Chromatographic analysis was performed on a Purospher RP-18e column (125×4.0 mm; 5.0 μm) equipped with a Purospher C18 precolumn (4.0×4.0 mm; 5.0 μm) (Merck Darmstadt, Germany), both thermostated at 30° C. Chromatogram recording was performed at 210 nm. The mobile phase used is composed of an 18:82 (v/v) $H_2O$:acetonitrile mixture eluted isocratically at a flow rate of 1 mL/min. Under the analysis conditions listed above, the retention time of PEA was found to be 4.6 min.

A preparation obtained according to Example 1 but not including the mannose derivative demonstrated similar solubility and rate of solubilization.

Example 3

Dimensional and Morphological Characterization of Particles

The nanostructured PEA suspension obtained according to Example 1 was analyzed by light scattering to assess the size of the nanoparticles.

The results are shown in Table III below.

TABLE III

| | Raw PEA | PEA Example 1 |
|---|---|---|
| Size (nm ± SD) | Macro and microscopic flakes | 261.6 ± 68.11 nm |

Morphologically, scanning electron microscopy (SEM) analyses of both forms were performed. From the images in FIG. 2, it may be seen that PEA in raw form is shown to be in the form of irregular macroscopic agglomerates (a few tens of microns), whereas nanostructured PEA according to the present invention is shown to comprise distinct nanometer formations.

A preparation obtained according to Example 1 but not including the mannose derivative has been characterized and the results are similar to those of Example 3.

Example 4

Comparative Assays

Following the process of Example 1, similar formulations were prepared, but omitting certain components one by one:

1) absence of squalene, 2) replacement of squalene with squalane

3) Absence of step 1 and 2 surfactants.

Figure 3:
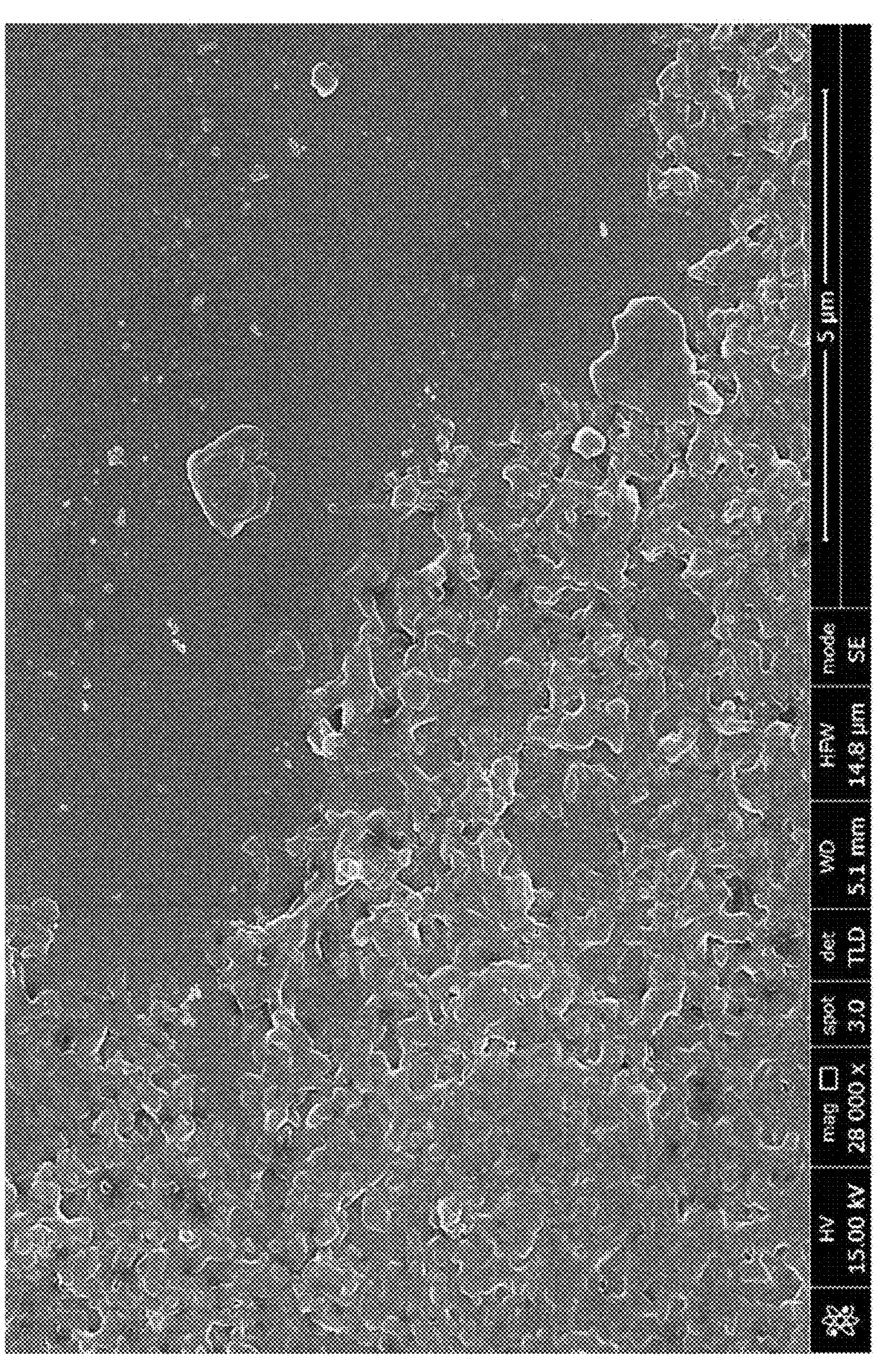
FIG. 3 shows a scanning electron microscope image (28,000× magnification) of a formulation in the absence of squalene.

1) Tests conducted showed that in the absence of squalene the formulation appears to be unstable and without visible macroscopic aggregates; however, by SEM analysis (see FIG. 3) the absence of well-defined nanostructures and the presence of microscopic aggregates are observed. The PEA solubilization rate in a 1% sodium cholate solution in this formulation is found to be 15.52 μg/m after 30 min (see Table 1).

Figure 5:
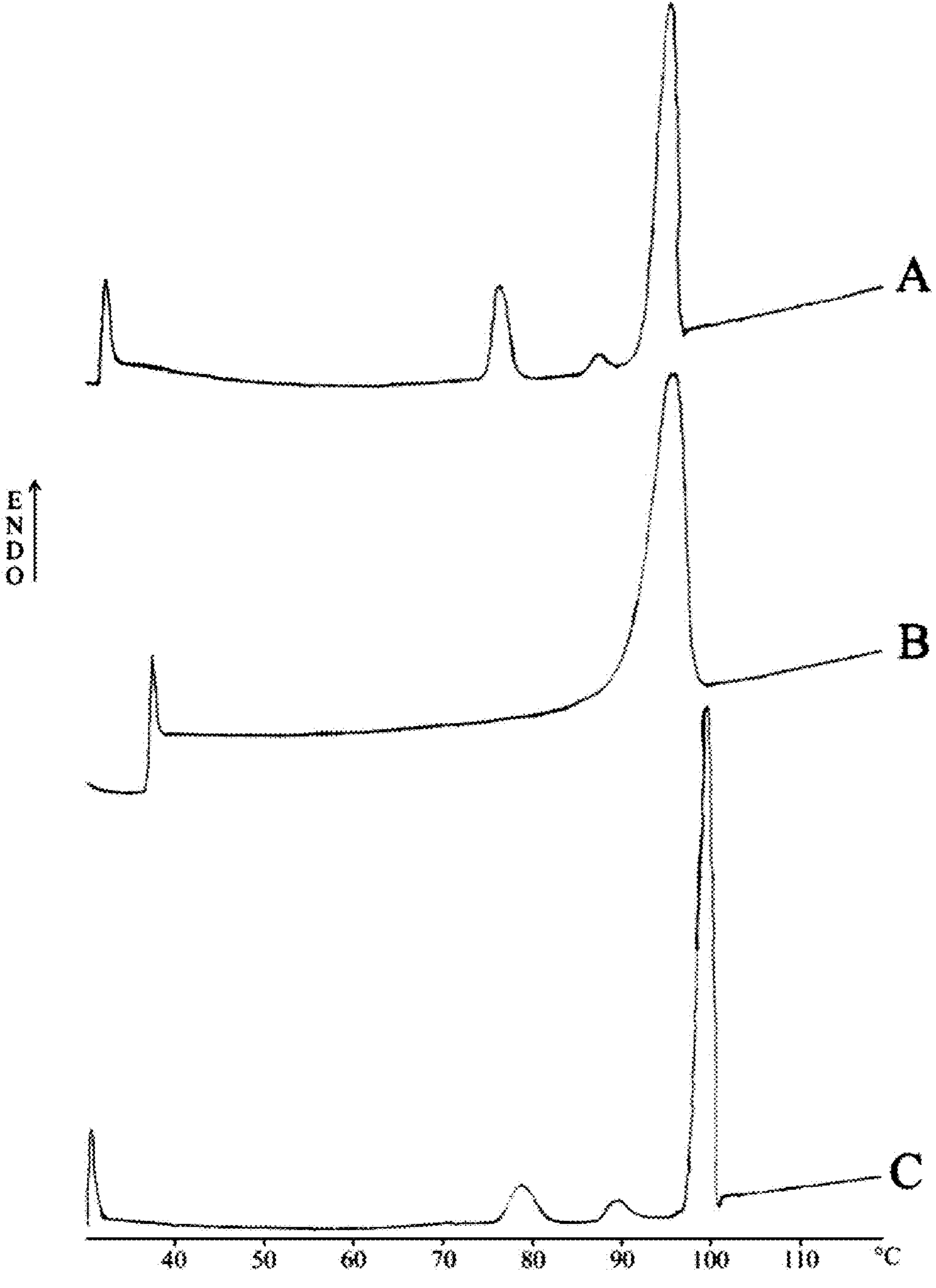
FIG. 5 shows thermograms obtained by differential scanning calorimetry of the PEA:squalane mixture in ethanol (A), the PEA:squalene mixture in ethanol (B), and raw PEA in ethanol (C).

2) The use of the hydrogenated form of squalene, squalane, does not allow the same obtainment of nanostructured PEA assuming a selective affinity between PEA and squalene. This is confirmed by DSC analysis (FIG. 5) of mixtures prepared in alcoholic solution as per example 1 of PEA+squalane and PEA+squalene where in the former case the three polymorphic forms of PEA are present, as in the case of raw PEA, while in the latter case there is stabilization of a single form, the metastable polymorph II.

Figure 4:
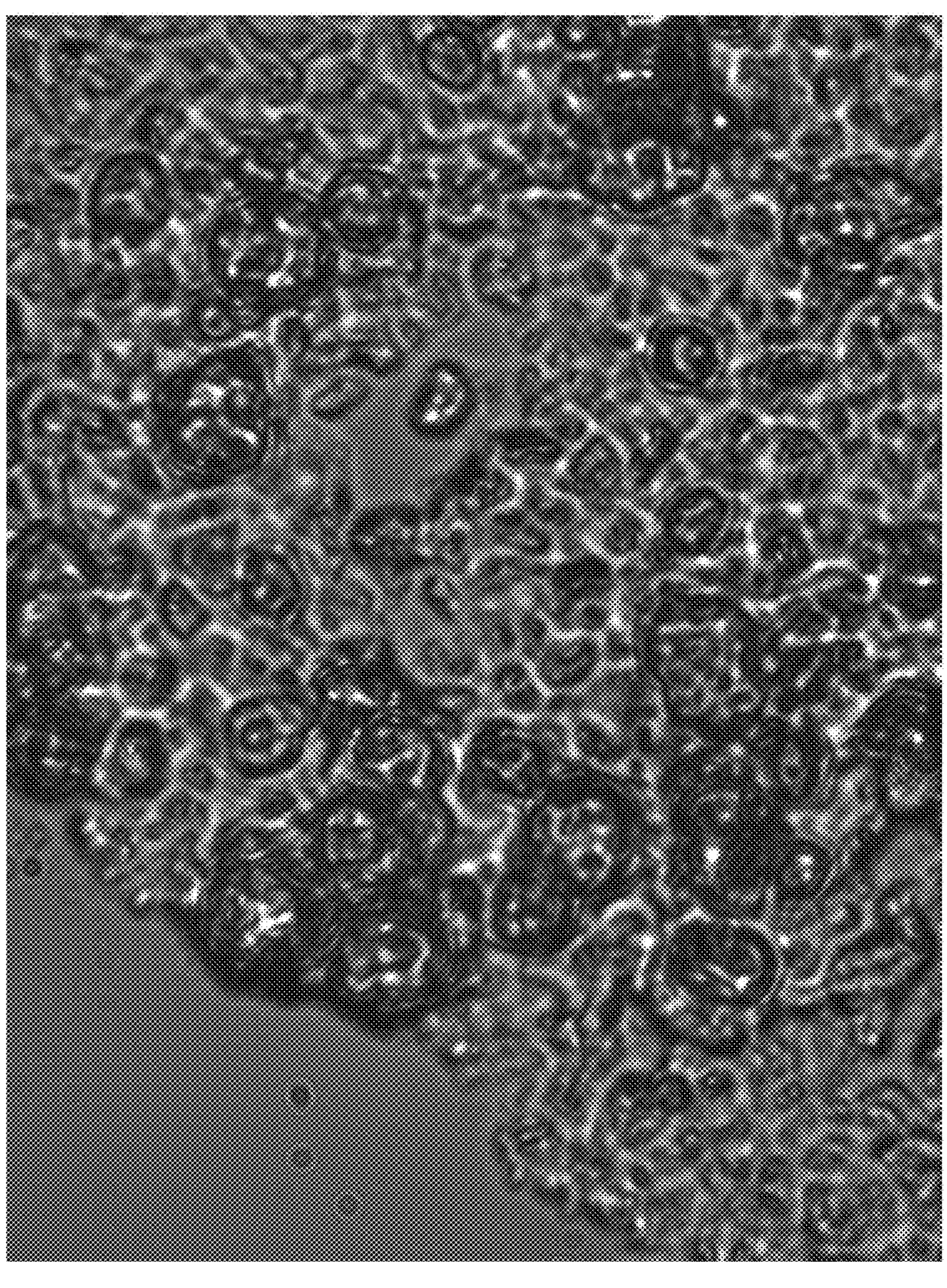
FIG. 4 shows an optical microscope image (400× magnification) of a formulation in the absence of surfactants.

3) Tests conducted showed that, in the absence of the first and second surfactants, the formulation appears unstable. Macroscopic aggregates indicative of non-obtainment of nanostructured PEA are visible both with an optical microscope (see FIG. 4) and the naked eye.

Example 5

Treatment of Animal Model with Psoriasis

A mouse model of psoriasis (8-week-old C57bl/6 female) was used in a preliminary study to compare the activity of nanostructured PEA with raw PEA and a commercial corticosteroid drug. Nanostructured PEA and raw PEA were added separately into an oil-in-water base cream comprised mainly of almond oil, vegetable emulsifier, and caprylic/capric triglyceride. Psoriasis was induced by Imiquimod, a compound widely used in preclinical drug development because of its ease of use, convenience, and production of skin phenotypes similar to acute psoriasis, including erythema, scale formation, and epidermal thickening. Specifically, treatment began after 2 days of Imiquimod application. The different creams were applied daily to the animals' backs for 8 days. Animals were divided into 5 groups: (1) vehicle cream, (2) vehicle cream+raw PEA 0.4%, (3) vehicle cream+nanostructured PEA 0.4%, (4) vehicle cream+nanostructured PEA 0.8%, and (5) betamethasone dipropionate cream, a commercial corticosteroid product.

Figure 6:
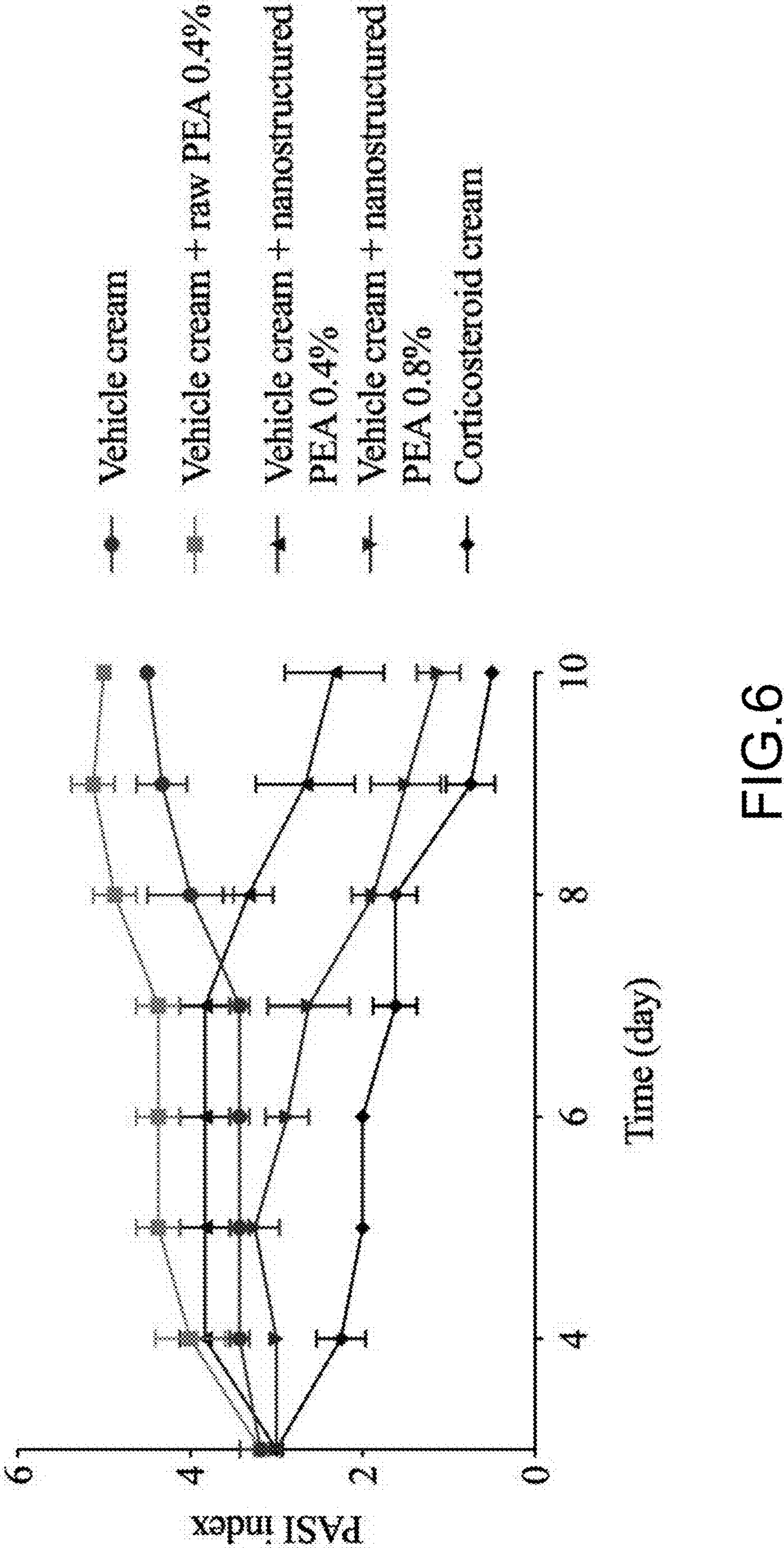
FIG. 6 shows the inherent graph of the PASI (Psoriasis Area Severity Index) calculated by summing the scores of erythema, scaling, and thickness of the 5 treatment groups.

Throughout the duration of the study (10 days), the mice were monitored daily, assessing various indicators such as stress, weight loss, loss of appetite, and reduced mobility. No alteration in these indicators was identified, except in group (5), in which the first signs of distress appeared in the last two days of treatment, probably due to the initial toxicity of the corticosteroid drug. As indicative parameters of psoriasis, erythema, desquamation, and lesion thickness were assessed daily. For all these parameters, group 4 of the treated animals (nanostructured PEA 0.8%) was the only one to have values similar to those of the positive control group of animals (commercial corticosteroid drug). Finally, the PASI index was calculated (FIG. 6). PASI is the Psoriasis Area and Severity Index and is used in the clinical evaluation of psoriasis to monitor the degree of severity of psoriasis-like lesions. This index is calculated by averaging all values for plaque parameters measured during treatment, erythema, desquamation, and thickness, with electronic calipers. The group of animals that received the highest dose of nanostructured PEA (Group 4) responded very similarly to those that received corticosteroids (Group 5), without showing the slightest sign of adverse side effects.

Example 6

Treatment of Psoriatic Plaques

A suspension of nanostructured PEA obtained according to Example 1 was used for the preparation of a 0.2% topical nanostructured PEA cream.

The cream was applied to the skin of volunteers with mild psoriasis (approximately 15) applied twice daily for 15 days.

Figure 7:
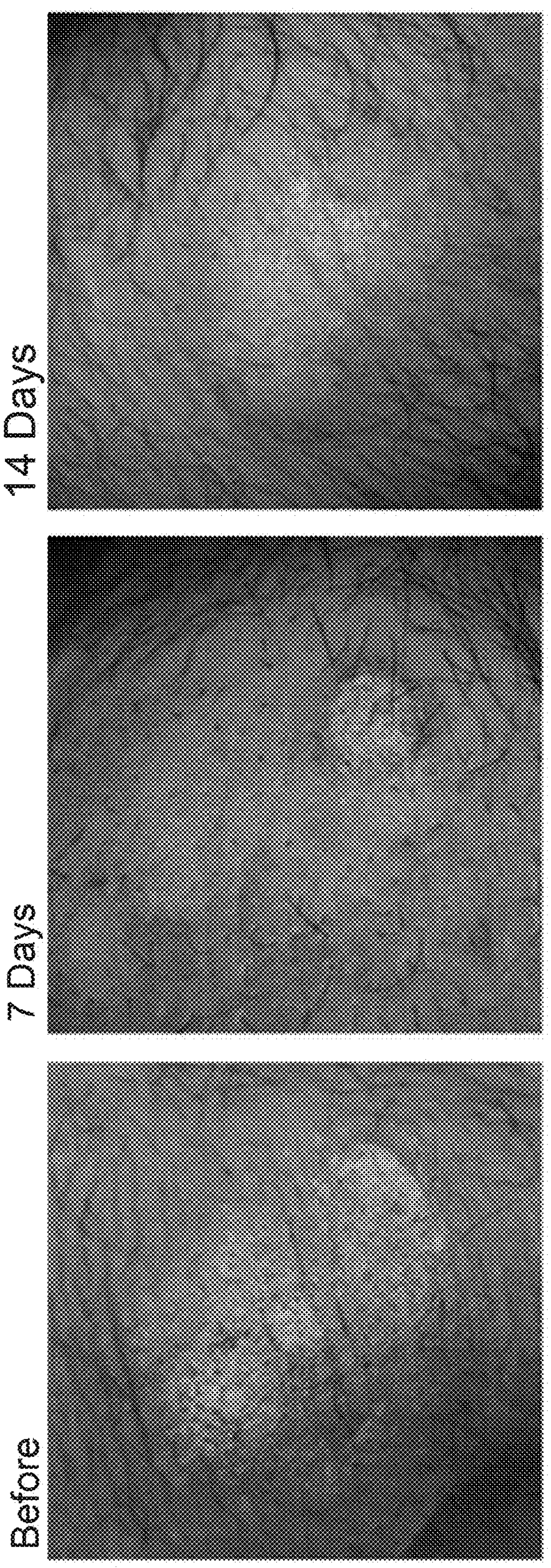
FIG. 7 shows a psoriatic plaque on a knee before, after 7 and after 14 days of treatment with a formulation of the invention.
Figure 8:
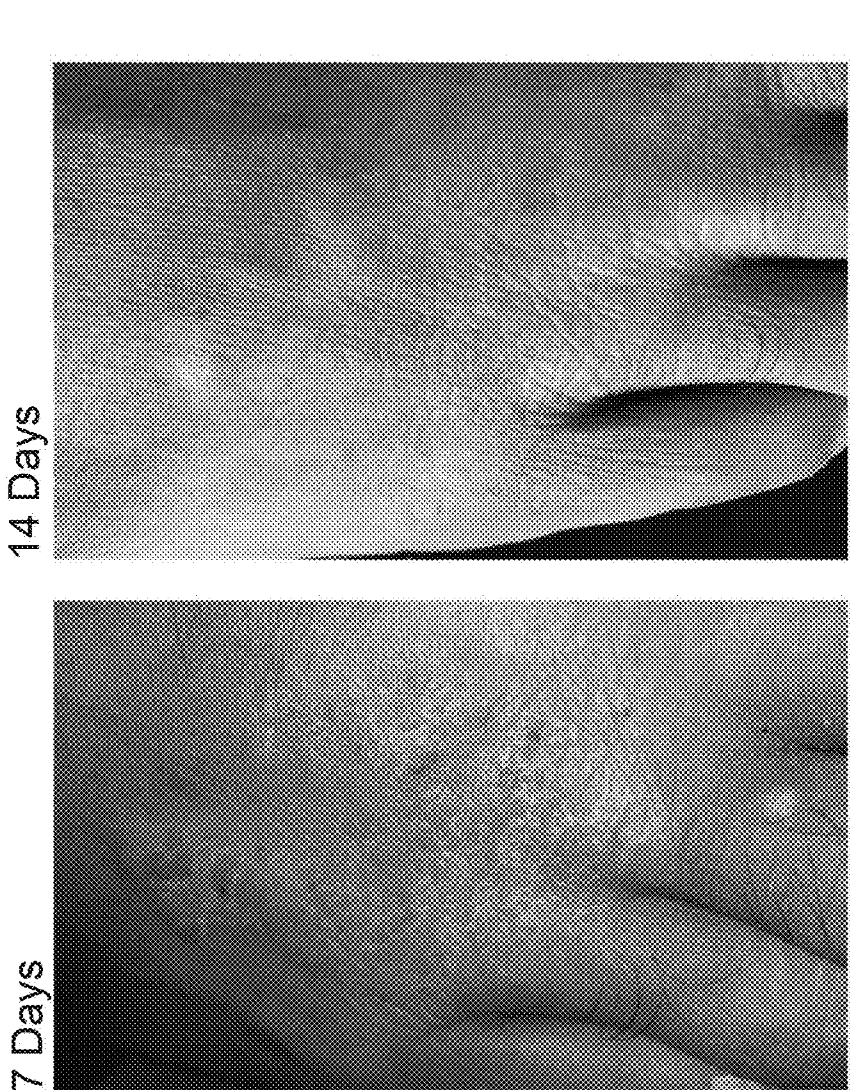
FIG. 8 shows the results of treating a psoriatic plaque on a foot before, after 7 and after 14 days of treatment with a formulation of the invention.
Figure 8:

Noticeable improvements in skin psoriatic plaques were noted after only 1 to 2 weeks, as shown by the images in FIG. 7, after application on knee, and in FIG. 8, after application on foot, as confirmed by the volunteers.

From the foregoing description, the many advantages of the present invention will be apparent to the person skilled in the art.

In particular, from a technological standpoint, the formulation of the invention is advantageously soluble in at least water and phosphate buffer at physiological pH, in the intestinal and pulmonary medium.

In addition to the above, the process described allows formulations to be obtained for the delivery of other and different active ingredients of a lipophilic nature, which otherwise cannot be administered, except with the known limitations and disadvantages.

The formulation obtained is of the nanostructured type and is not an emulsion; in effect, the components and the process for obtaining it differ from those of an emulsion, since they involve the use of a solvent miscible with water.

Furthermore, surprisingly, it has been noted that the use of squalene is not substitutable with other molecules, although very similar.

The invention claimed is:

1. A process for preparing a nanostructured suspension of palmitoylethanolamide (PEA), comprising the steps of:

1) dissolving said PEA in a water-miscible solvent in the presence of squalene and a first surfactant having HLB<10;
2) dripping the solution thus obtained in an aqueous phase in the presence of a second surfactant having HLB>10, wherein said PEA is a compound of the class of endocannabinoids, said first and said second surfactant are not surfactants having a steroidal structure;

thereby obtaining a suspension comprising nanoparticles made of PEA not having a carrier.

2. The process according to claim 1, wherein said water-miscible solvent is selected from the group consisting of ethanol, methanol, isopropanol, acetone, and acetonitrile.

3. The process according to claim 1, wherein in step 1) said surfactant is glycerylmonostearate or sorbitan monostearate.

4. The process according to claim 1, wherein in step 2) said second surfactant is selected from the group consisting of: a triterpenoid saponin, polysorbates, poloxamer, gelatin, polyethylene glycol, palmitate sucrose and mixtures thereof.

5. The process according to claim 1, wherein the surfactant of step 1) and the surfactant of step 2) are added in a total amount by weight so as to obtain a ratio of about 1:0.25-1:1.75 PEA:total surfactants.

6. The process according to claim 1, wherein in step 2) a compound is further added, wherein the compound is selected from the group consisting of: fucose in monomeric, oligomeric, or polymeric form; mannose in monomeric, oligomeric, or polymeric form; methyl alpha-D-mannopyranoside; fucosylated fatty acids; fucosylated proteins, fucosylated N-acetylglucosamine; mannosylated fatty acids; mannosylated proteins and mannosylated N-acetylglucosamine.

7. A nanostructured suspension obtained with a process for preparing a nanostructured suspension of palmitoylethanolamide (PEA), comprising the steps of 1) Dissolving PEA in a water-miscible solvent in the presence of squalene and a first surfactant having HLB<10; and
2) dripping the solution thus obtained in a aqueous phase in the presence of a second surfactant having HLB>10, thereby obtaining a suspension comprising nanoparticles made of PEA not having a carrier.

8. The nanostructured suspension according to claim 7, wherein said nanostructured suspension comprises nanoparticles characterized by a diameter of about 250-350 nm.

9. A pharmaceutical or nutraceutical or cosmetic preparation comprising the nanostructured suspension according to claim 7 in the form of a cream, gel, spray, emulsion, foam, dry powder or suspension for inhalation, capsule, tablet, granulate, suppository, eye drops, aqueous suspension or transdermal patch.

10. The nanostructured suspension of claim 7, wherein in step 1) said first surfactant is glycerylmonostearate or sorbitan monostearate.

11. The nanostructured suspension of claim 7, wherein in step 2) said second surfactant is selected from the group consisting of a triterpenoid saponin, polysorbates, poloxamer, gelatin, palmitate sucrose and a mixture thereof.

12. The nanostructured suspension of claim 7, wherein in step 2) a compound is further added, wherein the compound is selected from the group consisting of: fucose in monomeric, oligomeric, or polymeric form; mannose in monomeric, oligomeric, or polymeric form; methyl alpha-D-mannopyranoside; fucosylated fatty acids; fucosylated proteins, fucosylated N-acetylglucosamine; mannosylated fatty acids; mannosylated proteins; mannosylated N-acetylglucosamine and a mannosylated fatty acid.

13. A composition comprising nanoparticles made of PEA not having a carrier obtained by subjecting the nanostructured suspension of claim 7 to a drying step.

14. A pharmaceutical or nutraceutical or cosmetic preparation comprising the composition according to claim 13 in the form of a cream, gel, spray, emulsion, foam, dry powder or suspension for inhalation, capsule, tablet, granulate, suppository, eye drops, aqueous suspension or transdermal patch.

15. The pharmaceutical or nutraceutical or cosmetic preparation according to claim 9 further comprising an excipient that is suitable for pharmaceutical, nutraceutical, or cosmetic use.

16. The pharmaceutical or nutraceutical or cosmetic preparation according to claim 14 further comprising an excipient that is suitable for pharmaceutical, nutraceutical, or cosmetic use.

17. A method for treating a condition comprising administering a nanostructured suspension according to claim 7 to a patient suffering from the condition, wherein the condition is selected from the group consisting of: psoriasis, dermatitis, eczema, acne, folliculitis, pityriasis, pulmonary infection and inflammation, atherosclerosis, asthma, rheumatoid arthritis, multiple sclerosis, neurodegenerative disease, Crohn's disease, colitis, and glaucoma.

18. A method for treating a condition comprising administering a pharmaceutical or nutraceutical or cosmetic preparation according to claim 9 to a patient suffering from the condition, wherein the condition is selected from the group consisting of: psoriasis, dermatitis, eczema, acne, folliculitis, pityriasis, pulmonary infection and inflammation, atherosclerosis, asthma, rheumatoid arthritis, multiple sclerosis, neurodegenerative diseases, Crohn's disease, colitis, and glaucoma.

* * * * *